United States Patent [19]

Molloy et al.

[11] 4,336,269

[45] Jun. 22, 1982

[54] PARA-NITROPHENYLALKYLAMINES

[75] Inventors: Bryan B. Molloy, North Salem; Mitchell I. Steinberg, Indianapolis, both of Ind.

[73] Assignee: Eli Lilly and Company, Indianapolis, Ind.

[21] Appl. No.: 237,569

[22] Filed: Feb. 24, 1981

Related U.S. Application Data

[60] Division of Ser. No. 102,044, Dec. 10, 1979, Pat. No. 4,277,501, which is a continuation-in-part of Ser. No. 861,789, Dec. 19, 1977, abandoned.

[51] Int. Cl.³ .................. A61K 31/135; C07C 87/28
[52] U.S. Cl. ................................. 424/330; 564/374
[58] Field of Search ..................... 424/330; 564/374

[56] References Cited

U.S. PATENT DOCUMENTS

| | | | |
|---|---|---|---|
| 3,639,476 | 2/1972 | Eberle et al. | 260/520.8 R |
| 3,759,997 | 9/1973 | Napolitano | 260/570.8 R |
| 3,972,935 | 7/1974 | Molloy | 260/570 R |
| 4,049,827 | 10/1976 | Molloy | 424/330 |
| 4,219,568 | 8/1980 | Goldberg et al. | 424/330 |

FOREIGN PATENT DOCUMENTS 872832  6/1979  Belgium .

OTHER PUBLICATIONS

Chem. Abst., 7, 334(1913), Braun et al.
Chem. Abst., 54, 19588 (f–i) 1960, Morikawa.
Chem. Abst., 88, 50076 (s) 1978, Mutai et al.
Barlow et al., Pharmac. 37, 555–584 (1969).

*Primary Examiner*—Douglas W. Robinson
*Attorney, Agent, or Firm*—Charles W. Ashbrook; Arthur R. Whale

[57] ABSTRACT

Certain secondary and tertiary para-nitrophenylalkylamines are potent antiarrhythmic agents which prolong the action potential duration of cardiac tissue. A method of treating re-entrant arrhythmias, and pharmaceutical formulations containing paranitrophenylalkylamines, are provided.

9 Claims, No Drawings

PARA-NITROPHENYLALKYLAMINES

CROSS-REFERENCE TO RELATED APPLICATIONS

This is a division of Ser. No. 102,044 filed Dec. 10, 1979, now U.S. Pat. No. 4,277,501, which was a continuation-in-part of application Ser. No. 861,789, filed Dec. 19, 1977, now abandoned.

BACKGROUND OF THE INVENTION

Despite the extensive amount of research and the relatively large number of drugs devoted to the treatment of heart disease, mortality from cardiovascular disorders remains alarmingly high. Cardiovascular deterioration is known to commence early in life and is progressive throughout. It has been said that about half the population by the age of 50 have about fifty percent occlusion of at least one coronary artery, while less than about one-fifth have entirely unoccluded arteries at this age, Rissanen, *Advan. Cardiol.*, 4, 99 (1970).

The mechanism of action of various antiarrhythmic drugs generally is mediated by their effects upon the electrophysiological properties of cardiac muscle and conducting tissue. The electrical potential difference present in a heart muscle is created by ionic concentration differences across the membrane of the cardiac cell; the cardiac membrane being selectively permeable to different ionic species which pass through pores or channels. When the cardiac muscle is at rest, its interior is negatively charged due to a high intracellular concentration of non-diffusable large anions. During the action potential, the interior becomes positively charged relative to the exterior due to the sudden increase in sodium permeability resulting in the influx of positive charges. Then, until repolarization of the tissue takes place, the membranes are totally refractory to the passage of further sodium ions. The refractory period is quite long since repolarization is about 100 times slower than depolarization. Any drug which shortens the duration of the cardiac action potential thus necessarily shortens the refractory period and consequently increases the possibility of re-entrant rhythms under certain abnormal conditions. The refractory period would of course be prolonged if repolarization were delayed.

Various drugs have been used in the treatment of rhythm disorders. Quinidine, procaine amide, and lidocaine are perhaps among the best known and most widely used agents. All of such drugs act primarily by directly affecting membrane conductance so as to increase or decrease various ionic flows. A number of quaternary ammonium salts recently have been found useful in treating arrhythmia. Among such salts is a drug called bretylium (see U.S. Pat. No. 3,038,004). Bretylium is a salt of (o-bromobenzyl)ethyldimethylammonium cation. It has been shown to be effective in the treatment of disturbances of ventricular rhythm which are not successfully treated by other more conventional drugs, see Morgan et al., *J. Pharm. Sci.*, 65, 467 (1976). Unfortunately, it possesses many adverse side effects including sympathomimetic and sympathomyltic effects.

Several investigators recently have been interested in developing quaternary ammonium compounds which are useful antiarrhythmic and antifibrillatory drugs which at the same time cause no adverse effects on the autonomic nervous system (see particularly Lucchesi et al., "Pharmacological Modification of Arrhythmias After Experimentally Induced Acute Myocardial Infarction" American Heart Association Monograph No. 47, December, 1975). The dimethyl quaternary ammonium salt of propranolol has demonstrated useful antiarrhythmic activity against a variety of experimentally induced cardiac arrhythmias, Schuster et al., *J. Pharmacol. Exp. Ther.*, 184, 213 (1973) and Kniffen et al., *J. Pharmacol. Exp. Ther.*, 187, 260 (1973).

Our co-pending application embraces quaternary ammonium compounds, and more specifically phenylbutyl and phenylpropylammonium salts. We have now found that a unique group of para-nitrophenyl alkylamines, which are predominantly tertiary amines, are surprisingly almost equipotent with the corresponding quaternarized salt. It therefore is an object of this invention to provide certain para-nitrophenylalkyl amines which are unexpectedly potent antiarrhythmic agents.

SUMMARY OF THE INVENTION

This invention relates to specific and potent antiarrhythmic drugs which are useful in preventing ventricular fibrillation and other re-entrant arrhythmias by selectively prolonging the action potential, and consequently the refractoriness, of cardiac tissue. The invention additionally is directed to a method of prolonging the action potential of cardiac tissue and thus preventing and treating ventricular fibrillation and related re-entrant arrhythmias. The invention also provides pharmaceutical formulations useful in the treatment of cardiac arrhythmia.

The decrease in the rate of rise of the action potential caused by many of the commonly used cardiovascular drugs results in conduction depression in the intact heart. This action, in conjunction with the shortened refractory period, may predispose the heart to a variety of re-entrant arrhythmias, including ventricular fibrillation and flutter, the most serious forms of arrhythmia.

The compounds of this invention are particularly potent in prolonging both the action potential and refractory period of cardiac tissue. Moreover, they are selective in their activity in that they cause no inhibition of the rate of rise of the action potential at concentrations that prolong refractoriness. The compounds of this invention therefore are useful in the treatment and prevention of a variety of arrhythmias which have as their basis single or multiple re-entrant rhythms. The compounds typically will be used in the treatment of arrhythmias such as ventricular flutter, ventricular fibrillation, ventricular preexcitation, atrial fibrillation, and supraventricular tachycardia.

The compounds provided by this invention are para-nitrophenylalkylamines defined by the formula

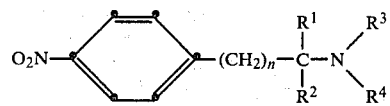

wherein:
n is 2–5;
$R^1$ is hydrogen or $C_1$–$C_2$ alkyl;
$R^2$ is hydrogen or $C_1$–$C_3$ alkyl;
$R^3$ is hydrogen or $C_1$–$C_8$ alkyl;
$R^4$ is $C_1$–$C_{10}$ alkyl;
provided that when $R^3$ is hydrogen, $R^4$ is $C_5$–$C_7$ alkyl, and the pharmaceutically acceptable acid addition salts thereof.

A preferred group of compounds are those wherein $R^4$ is $C_2$–$C_{10}$ alkyl.

Further preferred compounds provided by this invention are those defined by the above formula wherein n is 3 or 4, and most preferably wherein n is 3.

Additionally preferred compounds have the above formula wherein $R^4$ is $C_3$–$C_{10}$ alkyl, more preferably $C_5$–$C_{10}$ alkyl, and especially $C_5$–$C_8$ alkyl.

The most preferred compounds are those wherein n is 3, $R^1$ and $R^2$ both are hydrogen, and $R^4$ is $C_5$–$C_8$ alkyl.

A further embodiment of this invention comprises a method of treating re-entrant arrhythmias and preventing the development thereof in humans which comprises administering to a subject suffering from such arrhythmia and in need of treatment or to a subject suspected of developing a re-entrant arrhythmia an antiarrhythmically effective dose of a compound of the above general formula.

A particularly preferred method of treatment comprises administering a compound of the above formula wherein n is 3 or 4, especially wherein n is 3.

A further preferred method of treatment comprises administering a compound of the above formula wherein $R^4$ is $C_3$–$C_{10}$ alkyl, ideally $C_5$–$C_{10}$ alkyl, and most preferably $C_5$–$C_8$ alkyl.

The most preferred method of treatment comprises administering a compound of the above formula wherein n is 3, $R^1$ and $R^2$ both are hydrogen, and $R^4$ is $C_5$–$C_8$ alkyl. A typically preferred compound to be administered is N-ethyl-N-n-hepty-4-(4-nitrophenyl)-butylamine, generally as an acid addition salt.

Still another embodiment of this invention is a pharmaceutical formulation useful in the treatment of cardiac arrhythmias comprising a compound of the above formula in combination with a pharmaceutical diluent, excipient or carrier therefor. A preferred formulation comprises a compound of the above formula wherein n is 3 or 4, especially wherein n is 3, and a carrier therefor. Additionally preferred formulations are those wherein $R^4$ is $C_3$–$C_{10}$ alkyl, ideally $C_5$–$C_{10}$ alkyl, and most preferably $C_5$–$C_8$ alkyl. The most preferred formulations are those wherein n is 3, $R^1$ and $R^2$ both are hydrogen and $R^4$ is $C_5$–$C_8$ alkyl.

DETAILED DESCRIPTION OF THE INVENTION

In the above formula $R^1$ represents hydrogen or a $C_1$–$C_2$ alkyl group, namely methyl and ethyl. $R^2$ represents hydrogen as well as $C_1$–$C_3$ alkyl such as methyl, ethyl, isopropyl and n-propyl. $R^3$ defines a $C_1$–$C_8$ alkyl group. Such term includes groups such as methyl, ethyl, n-propyl, n-butyl, isopentyl, 2-methylbutyl, 2-methylpentyl, 1-ethylpentyl, n-heptyl, n-octyl, isooctyl, and the like. Similarly, $R^4$ represents $C_1$–$C_{10}$ alkyl such as methyl, ethyl, n-pentyl, isohexyl, 2-ethylheptyl, n-heptyl, 3-methylheptyl, 1,2-dimethylheptyl, 1,2-dimethyloctyl, 1,1-dimethylheptyl, n-nonyl, n-decyl, and related alkyl groups.

The compounds of this invention are amines, both secondary and tertiary. As such, they are basic in nature and accordingly react with any of a number of inorganic and organic acids to form pharmaceutically acceptable acid addition salts. Acids commonly used to form such salts include hydrochloric, hydrobromic, sulfuric, para-toluenesulfonic, methanesulfonic, oxalic, phosphoric, p-bromophenylsulfonic, carbonic, succinic, citric, benzoic, acetic and related acids. Preferred pharmaceutically acceptable acid addition salts include those formed with hydrochloric acid, hydrobromic acid, phosphoric acid, oxalic acid, and para-toluenesulfonic acid.

The para-nitrophenylalkyl amines provided by this invention can be prepared by any of a number of art recognized chemical processes. A typical process, for instance, comprises first acylating a primary or secondary amine to form the corresponding amide, and then reducing the amide by reaction with any of a number of reducing agents, including borane or diborane, sodium borohydride, aluminum hydride, and the like. For example, an amine such as N-ethyl-n-hexylamine can be reacted with a para-nitrophenylalkanoyl halide, such as para-nitrophenylpropanoyl chloride, to form the corresponding amide. Reduction of the amide affords the corresponding amine of this invention. As an alternative, an amine such as 4-(4-nitrophenyl)butylamine can be acylated with a $C_1$–$C_8$ alkyl acylating agent such as n-pentanoyl bromide to provide the corresponding amide, which when reduced gives a secondary amine. Further acylation with a suitable $C_1$–$C_{10}$ acylating agent, followed by reduction, gives a tertiary amine of the invention.

The secondary and tertiary amines of this invention can alternatively be prepared by simple alkylation of a primary or secondary amine. For example, reaction of a secondary amine such as N-ethyl-4-(4-nitrophenyl)-butylamine with an alkylating agent such as n-heptyl iodide effects alkylation to give the corresponding tertiary amine, namely N-ethyl-N-n-heptyl-4-(4-nitrophenyl)butylamine.

Still another way to prepare the para-nitrophenylalkylamines of this invention comprises aromatic nitration of a phenylalkylamine. For instance, an unsubstituted phenylalkylamine such as N,N-di-n-hexyl-5-phenylpentylamine can be reacted with a mixture of nitric acid and sulfuric acid to effect nitration of the aromatic ring and thus provide a compound of the invention, namely N,N-di-n-hexyl-5-(4-nitrophenyl)pentylamine.

When a tertiary amine wherein one of the alkyl groups is methyl is desired, a particularly convenient method of preparation comprises reacting the appropriate primary or secondary amine with formaldehyde and formic acid. For example, reduction of an amide such as N-n-heptyl-3-(3-nitrophenyl)propionamide affords the corresponding N-n-heptyl-3-(3-nitrophenyl)propylamine. Reaction of the latter compound with formaldehyde and formic acid affords N-methyl-N-n-heptyl-3-(3-nitrophenyl)propylamine.

Still another method for preparing amines of this invention is by reductive amination of ketones. For example, compounds of the above formula wherein $R^1$ is hydrogen and $R^2$ is $C_1$–$C_3$ alkyl are best prepared by a procedure which coprises reacting a primary amine, i.e., an amine of the formula $R^4NH_2$, with a para-nitrophenylalkyl $C_1$–$C_3$ alkyl ketone. For instance, a ketone such as 2-(4-nitrophenyl)ethyl n-propyl ketone can be reacted with isooctylamine in the presence of hydrogen and a suitable catalyst such as sodium cyanoborohydride to effect condensation and reduction to provide N-isooctyl-1-n-propyl-3-(4-nitrophenyl)-propylamine. Further alkylation of such amine, if desired, provides a tertiary amine compound of this invention.

As already pointed out, the para-nitrophenylalkylamines of this invention readily react with inorganic and organic acids to form pharmaceutically acceptable acid addition salts. Typically, an amine will be dissolved in an unreactive organic solvent such as diethyl ether or ethyl acetate, and an equimolar quantity or an excess of a suitable acid will be added. The salt that forms normally is highly crystalline and precipitates out of solution, and is readily isolated by filtration. Further purification can be accomplished by recrystallization from common solvents such as ethanol, ethyl acetate, toluene and the like. If desired, the acid addition salt can be converted back to the free amine base by reaction with a base such as sodium hydroxide.

The following list of para-nitrophenylalkylamines is illustrative of the compounds comprehended by this invention. The listing is by no means inclusive and should not be so construed.

N-methyl-N-isopropyl-3-(4-nitrophenyl)propylamine;
N-ethyl-N-n-butyl-3-(4-nitrophenyl)propylamine;
N-n-heptyl-3-(4-nitrophenyl)propylamine;
N-n-propyl-N-n-heptyl-4-(4-nitrophenyl)butylamine;
N-ethyl-N-(3-methylhexyl)-5-(4-nitrophenyl)pentylamine;
N,N-di-n-hexyl-6-(4-nitrophenyl)hexylamine;
N,N-diethyl-1,1-dimethyl-5-(4-nitrophenyl)pentylamine;
N-n-decyl-N-n-heptyl-1-ethyl-4-(4-nitrophenyl)butylamine;
N-(2-methylbutyl)-3-(4-nitrophenyl)propylaminium chloride;
N-(3-ethylpentyl)-5-(4-nitrophenyl)pentylaminium phosphate;
N-ethyl-N-n-octyl-6-(4-nitrophenyl)hexylamine;
N,N-di-n-propyl-4-(4-nitrophenyl)butylaminium benzoate;
N-methyl-N-n-pentyl-4-(4-nitrophenyl)butylaminium tartrate;
N-isopropyl-N-n-hexyl-5-(4-nitrophenyl)pentylamine;
N-isobutyl-N-n-heptyl-4-(4-nitrophenyl)butylamine;
N-ethyl-N-n-heptyl-4-(4-nitrophenyl)butylamine;
N-ethyl-N-n-octyl-4-(4-nitrophenyl)butylaminium oxalate;
N-n-pentyl-N-n-octyl-5-(4-nitrophenyl)pentylaminium bromide;
N-n-butyl-N-n-decyl-6-(4-nitrophenyl)hexylamine;
N-isopentyl-N-n-hexyl-3-(4-nitrophenyl)propylaminium iodide;
N-n-hexyl-N-n-heptyl-5-(4-nitrophenyl)pentylamine;
N,N-di-n-heptyl-5-(4-nitrophenyl)pentylaminium sulfate;
N,N-di-n-propyl-1-methyl-5-(4-nitrophenyl)pentylamine;
N,N-diisopropyl-1-ethyl-5-(4-nitrophenyl)pentylamine;
N-ethyl-N-(3-methylhexyl)-1-n-propyl-5-(4-nitrophenyl)pentylamine;
N,N-di-n-pentyl-6-(4-nitrophenyl)hexylamine; and
N,N-diethyl-1-methyl-6-(4-nitrophenyl)hexylaminium bromide.

It should be noted that certain of the compounds of this invention have an asymmetric center and accordingly exist as optical isomers. For example, compounds of the above formula wherein $R^1$ and $R^2$ are different exist as a d-isomer, an l-isomer, and as the racemic mixture. Such compounds generally are utilized as a racemic mixture, however separation of such mixture into the optically active isomers can be readily accomplished if desired. Such separation is accomplished by forming a diastereomer by reaction of an amine precursor with an optically active substrate, separating the diastereomers by routine methods such as crystallization, and then cleaving the optically active substrate. A typical resolution, for instance, comprises reacting an amine such as dl-1-ethyl-3-(4-nitrophenyl)propylamine with optically active d or l α-methylbenzyl bromide. Repeated crystallization of the product to provide the separated diastereomers, followed by de-benzylation by hydrogenolysis, provides optically active d and l 1-ethyl-3-(4-nitrophenyl)propylamine. The latter compound can then be further alkylated if desired by the methods hereinabove described.

As already pointed out, the compounds of this invention are useful in treating and preventing re-entrant arrhythmias are particularly important due to their potent and selective ability to prolong the action potential duration of cardiac tissue. The compounds of the invention accordingly are useful in the treatment of arrhythmia by decreasing the vulnerability of the heart to re-entrant rhythms and ventricular fibrillation by prolonging the time of electrical systole. Since the compounds enhance the electrical stability of the heart, they are useful in combination with external electrical devices intended to terminate tachyarrhythmias, for instance ventricular tachycardia and ventricular fibrillation.

The activity of the compounds of this invention has been analyzed by utilizing standard electrophysiological techniques to measure resting potential, action potential amplitude, duration, rate of rise and effective refractory periods of normal canine Purkinje fibers superfused in vitro with Ringer solution at 35° C. and stimulated at 1 Hz. For example, N-ethyl-N-n-heptyl-4-(4-nitrophenyl)butylamine, at a concentration of $2.5 \times 10^{-9}$ molar, effected a twenty percent prolongation of action potential duration in Purkinje fibers that were driven at a constant frequency of 1 Hz. Similarly, N-methyl-N-n-heptyl-1-methyl-4-(4-nitrophenyl)-butylamine caused a twenty percent prolongation at a concentration of only $2 \times 10^{-9}$ molar.

Table I which follows presents similar data for a number of the compounds of the invention. The data presented is the effective dose, presented as molar concentration, of test compound required to effect a twenty percent prolongation of action potential duration of Purkinje fibers ($ED_{20}$).

TABLE I

| Test Compound | $ED_{20}$ molar concentration |
|---|---|
| N-ethyl-N-n-pentyl-4-(4-nitrophenyl)butylamine | $2.5 \times 10^{-8}$ |
| N-n-propyl-N-n-hexyl-4-(4-nitrophenyl)butylamine | $6.0 \times 10^{-9}$ |
| N-methyl-N-n-heptyl-4-(4-nitrophenyl)butylamine | $1.1 \times 10^{-8}$ |
| N-n-butyl-N-n-heptyl-4-(4-nitrophenyl)butylamine | $4.4 \times 10^{-9}$ |
| N-n-heptyl-4-(4-nitrophenyl)butylamine | $3.8 \times 10^{-8}$ |
| N,N-di-n-butyl-4-(4-nitrophenyl)butylamine | $7.5 \times 10^{-8}$ |
| N-ethyl-N-n-heptyl-1-methyl-4-(4-nitrophenyl)-butylamine | $4 \times 10^{-8}$ |

There is also provided by this invention a method for treating arrhythmia which comprises administering to a subject suffering from an arrhythmia and in need of treatment or to a subject suspected of developing an arrhythmia an effective amount for treating such arrhythmia of a compound of this invention. The compounds provided herein are effective in converting flutter, ventricular fibrillation, or rapid tachycardia to normal sinus rhythm as a result of the prolongation of refractoriness. The compounds are useful in situations where rapid inappropriate ventricular rates are present, particularly in cases of ventricular preexcitation tachyarrhythmia. The compounds are preferably utilized for the control of re-entrant arrhythmias in humans and for the prevention of sudden death resulting from ventricular fibrillation. Accordingly it is contemplated that the compounds are best utilized in a prophylactic treatment.

The compounds can be administered either orally or parenterally, and for prophylactic treatment are best formulated for convenient oral administration. The particular dose of compound administered according to this invention will of course be determined by the particular circumstances surrounding the case, including the compound administered, the route of administration, the particular arrhythmia being treated, and similar considerations. A typical dose for prophylactic treatment, however, will contain from about 5.0 $\mu$g/kg. to about 500 $\mu$g/kg. of the active compound of this invention when administered orally. Preferred oral doses will be about 5.0 to about 200 $\mu$g/kg., ideally about 10 to about 50 $\mu$g/kg. For I.V. administration, the dose will be from about 1.0 $\mu$g/kg. to about 200 $\mu$g/kg., preferably about 5.0 $\mu$g/kg. to about 50 $\mu$g/kg. The compounds can alternatively be administered intramuscularly, transdermally, or by similar modes, including buccal seals and the like.

The compound to be administered can be formulated by admixing with any of a number of suitable pharmaceutical diluents and carriers such as lactose, sucrose, starch powder, cellulose, calcium sulfate, sodium benzoate and the like. Such formulations can be compressed into tablets or can be encapsulated into gelatin capsules for convenient oral administration. A gelatin capsule suited to oral administration for prophylactic treatment of heart disease may contain, for example, a compound of this invention such as N-ethyl-N-n-heptyl-4-(4-nitrophenyl)butylaminium bromide in the amount of about 1 to about 5 mg. Such formulation can be administered orally at the rate of about 1 or 2 capsules per day or more often as needed depending upon the particular condition and patient being treated.

For parenteral administration, a compound of this invention can be formulated for intramuscular or intravenous administration. In the case of treatment of a patient suffering from a severe cardiac arrhythmia, it may be desirable to administer a compound of the invention by intravenous infusion in order to effect a speedy conversion to a normal sinus rhythm. Such normal condition can then be maintained by oral administration.

For parenteral administration, the compounds of this invention are formulated with any of a number of pharmaceutically acceptable carriers and diluents to constitute an injectable liquid solution. Commonly used diluents and carriers include water or saline solution, buffered aqueous solutions, as well as dispersing and surface active agents if needed. It will also be noted that a compound of this invention can be administered in combination with other known antiarrhythmic drugs which have potent antiautomatic effects. Such drugs include aprindine, quinidine, propranolol and the like. The compounds can also be used in conjunction with electrical defibrillatory devices.

A typical formulation suited to intramuscular administration may contain a compound of this invention such as N,N-di-n-pentyl-4-(4-nitrophenyl)butylaminium methanesulfonate in the amount of about 10.0 to 50.0 mg., with or without another antiarrhythmic drug such as quinidine in the amount of about 100 to 200 mg., and a suitable solubilizing agent and sufficient sterile water to bring the volume to about 2 ml. Such formulation can be injected at a rate of 1 to 4 times per day or more often depending upon the particular condition of the patient being treated.

The present invention will now be more fully described in terms of typical working examples. The following discussions are to be taken as illustrative of the compounds comprehended by the invention, and are not to be construed as limiting the invention in any particular respect.

EXAMPLE 1

N,N-Dimethyl-4-(4-nitrophenyl)butylamine

Sixty-five milliliters of oxalyl chloride were reacted with 31.4 g. of 4-(4-nitrophenyl)butanoic acid in 300 ml. of toluene at reflux for three hours to provide, following evaporation of the solvent and excess oxalyl chloride, 21.2 g. of 4-(4-nitrophenyl)butanoyl chloride. The acid chloride so formed was dissolved in 250 ml. of diethyl ether, to which solution was added excess dimethylamine gas. The mixture was stirred for sixteen hours at 24° C., and then the solvent was removed by evaporation under reduced pressure to provide an amide as a solid.

The solid thus formed was added portion-wise over one hour to a stirred solution of 275 ml. of a 0.94 molar solution of borane in tetrahydrofuran. Following complete addition of the solid, the reaction mixture was heated at reflux for twelve hours, and then cooled to 0° C. in an ice bath. The reaction mixture was diluted by the dropwise addition of 75 ml. of 2 N hydrochloric acid. The reaction solvent was then removed by evaporation under reduced pressure, and the residue was dissolved in 100 ml. of concentrated hydrochloric acid and heated at reflux for one hour. The acidic mixture then was cooled and made alkaline by the addition of 5 N sodium hydroxide. The alkaline solution was extracted several times with diethyl ether, and the ethereal extracts were combined, washed with water and dried. Removal of the solvent by evaporation under reduced pressure afforded 18.4 g. of N,N-dimethyl-4-(4-nitrophenyl)butylamine. The amine thus formed was dissolved in diethyl ether containing hydrogen chloride, whereupon a solid precipitate formed. Crystallization of the precipitate from 150 ml. isopropanol afforded 18.1 g. of N,N-dimethyl-4-(4-nitrophenyl)-butylaminium chloride. M.P. 143°–145° C.

Analysis calc. for $C_{12}H_{19}ClN_2O_2$ Theory: C, 55.70; H, 7.40; N, 10.83. Found: C, 56.00; H, 7.59; N, 10.98.

EXAMPLES 2–6

By reacting the appropriate amine with a para-nitrophenylalkanoyl halide, followed by reduction of the amide with borane according to the method of Example 1, the following para-nitrophenylalkyl amines were prepared.

N,N-dimethyl-5-(4-nitrophenyl)pentylaminium tosylate. M.P. 122°–125° C.

Analysis calc. for $C_{20}H_{28}N_2O_5S$ Theory: C, 58.80; H, 6.91; N, 6.86. Found: C, 59.00; H, 6.69; N, 7.06.

N,N-Diethyl-4-(4-nitrophenyl)butylaminium oxalate. M.P. 102°–105° C.

Analysis calc. for $C_{16}H_{24}N_2O_6$ Theory: C, 56.46; H, 7.11; N, 8.23. Found: C, 56.67; H, 7.03; N, 8.27.

N,N-Di-n-butyl-4-(4-nitrophenyl)butylaminium oxalate. M.P. 124°–127° C.

Analysis calc. for $C_{20}H_{32}N_2O_6$ Theory: C, 60.59; H, 8.14; N, 7.07. Found: C, 60.84; H, 8.08; N, 7.09.

N,N-Di-n-pentyl-4-(4-nitrophenyl)butylaminium oxalate. M.P. 110°–111° C.

Analysis calc. for $C_{22}H_{36}N_2O_6$ Theory: C, 62.24; H, 8.55; N, 6.60. Found: C, 62.38; H, 8.54; N, 6.69.

N,N-Di-n-hexyl-4-(4-nitrophenyl)butylaminium oxalate. M.P. 90°–93° C.

Analysis calc. for $C_{24}H_{40}N_2O_6$ Theory: C, 63.69; H, 8.91; N, 6.19. Found: C, 63.39; H, 8.69; N, 6.02.

EXAMPLE 7

N-n-Pentyl-4-(4-nitrophenyl)butylaminium chloride n-Pentylamine was reacted with 4-(4-nitrophenyl)butanoyl chloride to provide the corresponding amide. Nine grams of N-n-pentyl-4-(4-nitrophenyl)butyramide were reacted with 96 ml. of a 1 molar solution of diborane in tetrahydrofuran to provide, following isolation as described in Example 1, 7.8 g. of N-n-pentyl-4-(4-nitrophenyl)butylamine. The amine was dissolved in diethyl ether and reacted with hydrogen chloride to afford, following crystallization from isopropanol, 5.8 g. of N-n-pentyl-4-(4-nitrophenyl)butylaminium chloride. M.P. 144°–146° C.

Analysis calc. for $C_{15}H_{25}ClN_2O_2$ Theory: C, 59.89; H, 8.38; N, 9.31. Found: C, 60.11; H, 8.14; N, 9.51.

EXAMPLES 8–9

The following secondary amines were prepared by the method of Example 7.

N-n-hexyl-4-(4-nitrophenyl)butylaminium tosylate. M.P. 129°–131° C.

Analysis calc. for $C_{23}H_{34}N_2O_5S$ Theory: C, 61.31; H, 7.62; N, 6.22. Found: C, 61.21; H, 7.49; N, 6.20.

N-n-Heptyl-4-(4-nitrophenyl)butylaminium chloride. M.P. 114°–117° C.

Analysis calc. for $C_{17}H_{29}ClN_2O_2$ Theory: C, 62.08; H, 8.89; N, 8.52. Found: C, 62.35; H, 8.63; N, 8.71.

EXAMPLE 10

N-Methyl-N-n-hexyl-4-(4-nitrophenyl)butylaminium oxalate

To a cold stirred solution of 2.0 g. of N-n-hexyl-4-(4-nitrophenyl)butylamine in 7 ml. of formic acid were added dropwise 7 ml. of 37% aqueous formaldehyde. The reaction mixture was heated to 95° C. and stirred at this temperature for sixteen hours. The reaction mixture next was cooled and acidified by the addition of 10 ml. of 4 N hydrochloric acid. The aqueous acid mixture was washed twice with diethyl ether, and then made alkaline by the addition of 5 N sodium hydroxide. The product was extracted into diethyl ether. The ethereal extracts were combined, washed with water and dried. Removal of the solvent by evaporation under reduced pressure provided 2.2 g. of N-methyl-N-n-hexyl-4-(4-nitrophenyl)butylamine. The amine was dissolved in ethyl acetate and treated with oxalic acid to give, after crystallization from isopropanol, 2.1 g. of N-methyl-N-n-hexyl-4-(4-nitrophenyl)butylaminium oxalate. M.P. 103°–105° C.

Analysis calc. for $C_{19}H_{30}N_2O_6$ Theory: C, 59.67; H, 7.91; N, 7.32. Found: C, 59.64; H, 7.92; N, 7.59.

EXAMPLE 11

Following the procedure of Example 10, N-n-heptyl-4-(4-nitrophenyl)butylamine was reacted with formic acid and formaldehyde to provide, following conversion to the oxalate salt, 1.9 g. of N-methyl-N-n-heptyl-4-(4-nitrophenyl)butylaminium oxalate. M.P. 95°–98° C.

Analysis calc. for $C_{20}H_{32}N_2O_6$ Theory: C, 60.59; H, 8.14; N, 7.07. Found: C, 60.89; H, 8.05; N, 6.98.

EXAMPLE 12

N,N-Dimethyl-6-(4-nitrophenyl)hexylaminium oxalate

To a cold stirred solution of 31 ml. of concentrated sulfuric acid containing 31 ml. of concentrated nitric acid were added dropwise over fifteen minutes 19.6 g. of N,N-dimethyl-6-phenylhexylamine. The reaction mixture was then warmed to 25° C. and stirred for one hour. The reaction mixture was next added to 100 g. of ice and made alkaline by the addition of 5 N sodium hydroxide. The alkaline solution was extracted several times with diethyl ether, and the ethereal extracts were combined, washed with water, and dried. Evaporation of the solvent provided 25.1 g. of the product as a red oil. The oil was reacted with picric acid in diethyl ether to afford the picrate salt, which was then reacted with aqueous sodium hydroxide to give the free amine base as a purified oil. The purified oil was dissolved in ethyl acetate and treated with oxalic acid to provide, after several recrystallizations from isopropanol, N,N-dimethyl-6-(4-nitrophenyl)hexylaminium oxalate. M.P. 94°–97° C.

Analysis calc. for $C_{16}H_{24}N_2O_6$ Theory: C, 56.46; H, 7.11; N, 8.23. Found: C, 56.26; H, 6.91; N, 8.36.

EXAMPLE 13

N-Ethyl-N-n-octyl-4-(4-nitrophenyl)butylaminium oxalate

To a stirred solution of 9.8 g. of N-n-octyl-4-(4-nitrophenyl)butylamine in 40 ml. of acetone and 40 ml. of water containing 7.0 g. of sodium carbonate were added dropwise over thirty minutes 60 ml. of a solution of 2.6 g. of acetyl chloride in acetone. The reaction mixture was stirred for sixteen hours at room temperature, and then the acetone was removed by evaporation under reduced pressure. The aqueous layer was diluted with additional water, and then extracted with diethyl ether. Evaporation of the ether from the extracts provided 8.3 g. of N-acetyl-N-n-octyl-4-(4-nitrophenyl)butylamine.

Reduction of the acylated amine was effected by reaction with diborane according to the procedure of Example 1. The reduced amine, N-ethyl-N-n-octyl-4-(4-nitrophenyl)butylamine, was converted to the oxalate salt by reaction with oxalic acid in ethyl acetate. After several recrystallizations from isopropanol there was recovered 3.9 g. of N-ethyl-N-n-octyl-4-(4-nitrophenyl)butylaminium oxalate. M.P. 105°–108° C.

Analysis calc. for $C_{22}H_{36}N_2O_6$ Theory: C, 62.29; H, 8.55; N, 6.60. Found: C, 62.15; H, 8.27; N, 6.76.

EXAMPLES 14–21

Following the procedure of Example 13, the appropriate N-alkyl-para-nitrophenylalkylamine was acylated to give an N-acyl-N-alkyl-para-nitrophenylalkylamine, which upon reduction provided the following N,N-dialkyl-para-nitrophenylalkylamines.

N-Ethyl-N-n-heptyl-[1-methyl-4-(4-nitrophenyl)-]butylaminium oxalate. M.P. 90°–91° C.

Analysis calc. for $C_{22}H_{36}N_2O_6$ Theory: C, 62.24; H, 8.55; N, 6.60. Found: C, 62.12; H, 8.65; N, 6.60.

N,N-di-n-heptyl-4-(4-nitrophenyl)butylaminium oxalate. M.P. 80°–82° C.

Analysis calc. for $C_{26}H_{44}N_2O_6$ Theory: C, 64.97; H, 9.23; N, 5.83. Found: C, 64.85; H, 9.11; N, 5.84.

N-Ethyl-N-n-pentyl-4-(4-nitrophenyl)butylaminium oxalate. M.P. 92°–94° C.

Analysis calc. for $C_{19}H_{30}N_2O_6$ Theory: C, 59.67; H, 7.91; N, 7.32. Found: C, 59.92; H, 7.85; N, 7.10.

N-Ethyl-N-n-hexyl-4-(4-nitrophenyl)butylaminium oxalate. M.P. 112°–113° C.

Analysis calc. for $C_{20}H_{32}N_2O_6$ Theory: C, 60.59; H, 8.14; N, 7.07. Found: C, 60.34; H, 7.90; N, 6.99.

N-n-Hexyl-N-n-propyl-4-(4-nitrophenyl)butylaminium oxalate. M.P. 110°–112° C.

Analysis calc. for $C_{21}H_{34}N_2O_6$ Theory: C, 61.44; H, 8.35; N, 6.82. Found: C, 61.64; H, 8.21; N, 7.04.

N-n-Heptyl-N-n-propyl-4-(4-nitrophenyl)butylaminium oxalate. M.P. 81°–83° C.

Analysis calc. for $C_{22}H_{36}N_2O_6$ Theory: C, 62.24; H, 8.55; N, 6.60. Found: C, 62.20; H, 8.30; N, 6.67.

N-n-Hexyl-N-n-butyl-4-(4-nitrophenyl)butylaminium oxalate. M.P. 106°–108° C.

Analysis calc. for $C_{22}H_{36}N_2O_6$ Theory: C, 62.24; H, 8.55; N, 6.60. Found: C, 61.97; H, 8.63; N, 6.40.

N-n-Heptyl-N-n-butyl-4-(4-nitrophenyl)butylaminium oxalate. M.P. 91°–93° C.

Analysis calc. for $C_{23}H_{38}N_2O_6$ Theory: C, 62.99; H, 8.73; N, 6.39. Found: C, 63.07; H, 9.03; N, 6.47.

EXAMPLE 22

N-Ethyl-N-n-heptyl-4-(4-nitrophenyl)butylaminium oxalate n-Heptylamine was reacted with 4-(4-nitrophenyl)butanoyl chloride to provide 29.3 g. of N-n-heptyl-4-(4-nitrophenyl)butyramide. The amide was reacted with diborane to afford 25.8 g. of N-n-heptyl-4-(4-nitrophenyl)butylamine. The amine was dissolved in 70 ml. of acetone and added in one portion to 70 ml. of water containing 18.5 g. of sodium carbonate. The aqueous reaction mixture was stirred while 14.4 ml. of acetyl chloride in 70 ml. of acetone was added dropwise over one hour. The reaction mixture was stirred at room temperature for sixteen hours following the addition, and then the mixture was concentrated by evaporation of the acetone solvent under reduced pressure. The aqueous layer was extracted with diethyl ether, and the ethereal extract was then washed with water, with 2 N hydrochloric acid, again with water, and finally with saturated sodium chloride solution. The solution was dried and the solvent was removed by evaporation under reduced pressure to give 28.78 g of N-acetyl-N-n-heptyl-4-(4-nitrophenyl)butylamine.

To a stirred solution of 260 ml. of 1 molar diborane in tetrahydrofuran were added dropwise over thirty minutes a solution of 28.78 g. of N-acetyl-N-n-heptyl-4-(4-nitrophenyl)butylamine in 100 ml. of tetrahydrofuran. The reaction mixture was then heated at reflux and stirred for sixteen hours. After cooling the mixture to room temperature, 100 ml. of 2 N hydrochloric acid were added, and then the tetrahydrofuran was removed by evaporation under reduced pressure. The acidic reaction mixture was diluted by the addition of 100 ml. of concentrated hydrochloric acid, and then the mixture was heated at reflux for thirty minutes. The reaction mixture was cooled to room temperature, made alkaline by the addition of 5 N sodium hydroxide, and the product was extracted into diethyl ether. The ethereal extracts were combined, washed with water, dried, and the solvent was removed by evaporation under reduced pressure to give 28.1 g. of N-ethyl-N-n-heptyl-4-(4-nitrophenyl)butylamine as an oil. The amine thus formed was converted to the oxalate salt. M.P. 113°–115° C.

Analysis calc. for $C_{21}H_{34}N_2O_6$ Theory: C, 61.44; H, 8.35; N, 6.82. Found: C, 61.65; H, 8.12; N, 6.76.

EXAMPLE 23

N-Ethyl-N-isopentyl-4-(4-nitrophenyl)butylaminium tosylate

Isopentylamine was reacted with 4-(4-nitrophenyl)butanoyl chloride to provide N-isopentyl-4-(4-nitrophenyl)butyramide, which when reduced by reaction with diborane afforded N-isopentyl-4-(4-nitrophenyl)butylamine. Reaction of the latter compound with acetyl chloride under the conditions of Example 22 gave N-acetyl-N-isopentyl-4-(4-nitrophenyl)butylamine. Reaction of 21.8 g. of N-acetyl-N-isopentyl-4-(4-nitrophenyl)butylamine with 220 ml. of 1 M diborane in tetrahydrofuran provided, after workup according to the method of Example 22, 19.8 g. of N-ethyl-N-isopentyl-4-(4-nitrophenyl)butylamine. Reaction of the amine with para-toluenesulfonic acid in ethyl acetate afforded N-ethyl-N-isopentyl-4-(4-nitrophenyl)butylaminium tosylate. M.P. 78°–80° C.

Analysis calc. for $C_{24}H_{36}N_2O_5S$ Theory: C, 62.04; H, 7.81; N, 6.03; S, 6.90. Found: C, 61.93; H, 7.51; N, 6.02; S, 7.11.

EXAMPLE 24

N,N-Di-n-propyl-4-(4-nitrophenyl)butylaminium tosylate

A solution of 1.3 g. of N,N-di-n-propyl-4-(4-nitrophenyl)butylamine, prepared by the procedure of Example 1, in 20 ml. of ethyl acetate containing 1.0 g. of para-toluenesulfonic acid was heated at reflux for two minutes and then cooled to −70° C. The crystalline precipitate which formed was collected by filtration, recrystallized from ethyl acetate and air dried to give 961 mg. of N,N-di-n-propyl-4-(4-nitrophenyl)butylaminium tosylate. M.P. 71°–74° C.

Analysis calc. for $C_{23}H_{34}N_2O_5S$ Theory: C, 61.31; H, 7.61; N, 6.22. Found: C, 61.21; H, 7.39; N, 5.95.

EXAMPLE 25

| Formulation for oral administration | |
|---|---|
| N-Ethyl-N-n-heptyl-4-(4-nitrophenyl)butylaminium chloride | 300 mg |
| Lactose | 300 mg |
| Corn starch | 300 mg |
| Corn starch paste | 50 mg |
| Calcium stearate | 5 mg |
| Dicalcium phosphate | 45 mg |

The active ingredient is mixed with the corn starch, lactose, and dicalcium phosphate. The corn starch paste is prepared as a 10 percent aqueous paste and is blended into the mixture to uniformity. The mixture then is blended with the calcium stearate and compressed into tablets or placed in gelatin capsules. Each dosage form will contain about 1.0 mg. of active ingredient, to be administered orally at the rate of 1 to about 3 times each day to a subject weighing about 70 kg. and in need of therapeutic or prophylactic treatment for re-entrant arrhythmias. Such oral formulation is well suited to subjects receiving treatment from electrical defibrillatory devices.

EXAMPLE 26

| Formulation for parenteral administration | |
| --- | --- |
| N-methyl-N-n-hexyl-3-(4-nitrophenyl)propylaminium phosphate | 100 mg |
| isotonic saline | 1000 ml |

The solution of the above ingredients is administered intravenously at the rate of 1 ml. per minute to a subject suffering from ventricular fibrillation.

We claim:

1. A method of treating arrhythmia comprising administering to a patient in need of said treatment a therapeutic or prophylactic antiarrhythmic amount of a compound of the formula

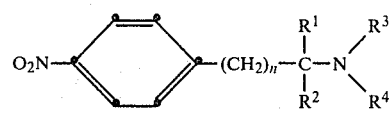

wherein:
n is 2–5;
$R^1$ is hydrogen or $C_1$–$C_2$ alkyl;
$R^2$ is hydrogen or $C_1$–$C_3$ alkyl;
$R^3$ is hydrogen or $C_1$–$C_8$ alkyl;
$R^4$ is $C_1$–$C_{10}$ alkyl;
provided that when $R^3$ is hydrogen, $R^4$ is $C_5$–$C_7$ alkyl, or a pharmaceutically acceptable acid addition salt thereof.

2. The method of claim 1 wherein n is 3 or 4.
3. The method of claim 2 wherein $R^4$ is $C_3$–$C_{10}$ alkyl.
4. The method of claim 2 wherein $R^4$ is $C_5$–$C_{10}$ alkyl.
5. The method of claim 2 wherein $R^4$ is $C_5$–$C_8$ alkyl.
6. The method of claim 1 wherein n is 3.
7. The method of claim 6 wherein $R^4$ is $C_3$–$C_{10}$ alkyl.
8. The method of claim 6 wherein $R^4$ is $C_5$–$C_{10}$ alkyl.
9. The method of claim 6 wherein $R^4$ is $C_5$–$C_8$ alkyl.

* * * * *